(12) United States Patent
Koehler et al.

(10) Patent No.: US 9,901,314 B2
(45) Date of Patent: Feb. 27, 2018

(54) ADJUSTABLE BOW-TIE FILTER FOR ACHIEVING OPTIMAL SNR IN HELICAL COMPUTED TOMOGRAPHY

(71) Applicant: KONINKLIJKE PHILIPS N.V., Eindhoven (NL)

(72) Inventors: Thomas Koehler, Norderstedt (DE); Roland Proksa, New Wulmstorf (DE)

(73) Assignee: Koninklijke Philips N.V., Eindhoven (NL)

( * ) Notice: Subject to any disclaimer, the term of this patent is extended or adjusted under 35 U.S.C. 154(b) by 120 days.

(21) Appl. No.: 14/910,068

(22) PCT Filed: Aug. 5, 2014

(86) PCT No.: PCT/IB2014/063700
§ 371 (c)(1),
(2) Date: Feb. 4, 2016

(87) PCT Pub. No.: WO2015/022599
PCT Pub. Date: Feb. 19, 2015

(65) Prior Publication Data
US 2016/0174917 A1 Jun. 23, 2016

Related U.S. Application Data

(60) Provisional application No. 61/865,273, filed on Aug. 13, 2013.

(51) Int. Cl.
*G21K 3/00* (2006.01)
*A61B 6/00* (2006.01)
*A61B 6/03* (2006.01)

(52) U.S. Cl.
CPC ............ *A61B 6/4035* (2013.01); *A61B 6/032* (2013.01)

(58) Field of Classification Search
CPC .. A61B 6/00; A61B 6/03; A61B 6/032; A61B 6/4035
(Continued)

(56) References Cited

U.S. PATENT DOCUMENTS 6,990,171 B2 1/2006 Toth et al.
7,082,189 B2 * 7/2006 Yahata ................. A61B 6/06
378/156
(Continued)

FOREIGN PATENT DOCUMENTS

EP 1498908 1/2005
WO 2009/083878 7/2009
(Continued)

OTHER PUBLICATIONS

Kohler, et al., "Beam shaper with optimized dose utility for helical cone-beam CT", Med. Phys. 38 (7), Jul. 2011.
(Continued)

*Primary Examiner* — Jurie Yun

(57) ABSTRACT

A filter assembly for use in a helical computed tomography system having an x-ray source for projecting x-ray beams along a projection axis is presented, the filter assembly including a first filter element for attenuating at least a portion of the x-ray beams, the first filter element constructed as a background-wedge for attenuating x-rays having a large aperture and a second filter element for attenuating at least a portion of the x-ray beams, the second filter element constructed to create a ridge. The second filter element may be rotated with respect to or adjusted in relation with or removed or replaced from the filter assembly to allow for adaptation to different helical pitch values.

20 Claims, 4 Drawing Sheets

(58) Field of Classification Search
USPC .................................. 378/156, 157, 158, 159
See application file for complete search history.

(56) References Cited

U.S. PATENT DOCUMENTS

| | | |
|---|---|---|
| 7,254,216 B2 | 8/2007 | Thandiackal et al. |
| 2012/0294414 A1 | 11/2012 | Koehler |

FOREIGN PATENT DOCUMENTS

| | | |
|---|---|---|
| WO | 2010/102908 | 9/2010 |
| WO | 2012/042484 | 4/2012 |
| WO | 2012/174246 | 12/2012 |

OTHER PUBLICATIONS

Liu, et al., "Dynamic Bowtie for Fan-beam CT", J Xray Sci Technol., 2013; 21(4):579-90.

\* cited by examiner

ADJUSTABLE BOW-TIE FILTER FOR ACHIEVING OPTIMAL SNR IN HELICAL COMPUTED TOMOGRAPHY

CROSS REFERENCE TO RELATED APPLICATIONS

This application is the U.S. National Phase application under 35 U.S.C. § 371 of International Application No. PCT/2014/063700 filed Aug. 5, 2014, published as WO 2015/022599 on Feb. 19, 2015, which claims the benefit of U.S. Provisional Patent Application No. 61/865,273 filed Aug. 13, 2013. These applications are hereby incorporated by reference herein.

BACKGROUND

Technical Field

The present disclosure relates to computed tomography (CT). More particularly, the present disclosure relates to x-ray filters for controlling the spatial intensity distribution of an x-ray beam in CT systems.

Description of Related Art

Computed tomography (CT) systems typically include an x-ray source collimated to form a fan beam directed through an object to be imaged, i.e., a patient, and received by an x-ray detector array. The x-ray source, the fan beam, and the detector array are oriented to be situated within the x-y plane of a Cartesian coordinate system, termed the "imaging plane." The x-ray source and the detector array may be rotated together on a gantry within the imaging plane, around the imaged object, and hence around the z-axis of the Cartesian coordinate system.

In CT systems, a device called a beam-shaper is generally used to minimize the x-ray radiation dose a patient receives. One of the ways to achieve this goal is to insert a bowtie-shaped piece of polymer, called a "wedge," in the path of the x-ray beam. The wedge, functioning as an x-ray attenuation filter, is generally a synthetic polymer, such as Teflon having an x-ray absorption spectral characteristic near that of water and hence the human body. The attenuation filter is intended to compensate for the variation in thickness of the imaged body. The x-rays that pass through the center of the imaged body, normally the thickest part, are least attenuated by this filter, whereas the x-rays that pass through the edges of the imaged body, normally the thinnest part, are more attenuated by this filter. The result of this selective attenuation is that the x-rays impinging on the detectors have a similar intensity. The attenuation filter may therefore allow use of more sensitive x-ray detectors reducing the range of x-ray intensities.

An issue with radiology today is how to reduce radiation doses during CT scans without compromising image quality and robustness with respect to patient motion. Therefore, there is an increasing need to develop filters for modulating incoming intensity of an x-ray beam.

SUMMARY

In accordance with aspects of the present disclosure, a filter assembly is presented. The filter assembly includes a first filter element for attenuating at least a portion of the x-ray beams, the first filter element constructed as a background-wedge for attenuating x-rays having a large aperture and a second filter element for attenuating at least a portion of the x-ray beams, the second filter element constructed to create a ridge.

According to an aspect of the present disclosure, the second filter element is rotated. Rotation of the second filter element allows for adaptation to different helical pitch values.

According to a further aspect of the present disclosure, the first filter element remains stationary or can be removed completely from the beam for adaptation to axial scanning.

According to another aspect of the present disclosure, the first and second filter elements are positioned between the x-ray source and a detector for reconstructing an object onto which the x-ray beams are projected upon. Reconstruction occurs with one or more reconstruction algorithms.

According to yet another aspect of the disclosure, the first and second filter elements combine to form a substantially bow-tie shaped filter.

According to a further aspect of the disclosure, the first and second filter elements result in a partitioning of mean weights of the x-ray beams projected onto an object.

In accordance with aspects of the present disclosure, a filter assembly is presented. The filter assembly includes a first filter layer having a first shape and a second filter layer having a second shape, the second shape being different than the first shape. The second filter layer is adapted and dimensioned to rotate to accommodate a plurality of different helical pitch values.

According to yet a further aspect of the disclosure, a method for reducing radiation exposure when using a helical computed tomography (CT) system is presented. The method includes the steps of positioning a first filter element and a second filter element between a patient and an x-ray source emitting x-ray beams; attenuating a portion of the x-ray beams via the first filter element, the first filter element being a background-wedge for attenuating x-ray beams having a large aperture; and attenuating a portion of the x-ray beams via a second filter element, the second filter element configured to create a ridge.

Further scope of applicability of the present disclosure will become apparent from the detailed description given hereinafter. However, it should be understood that the detailed description and specific examples, while indicating preferred embodiments of the present disclosure, are given by way of illustration only, since various changes and modifications within the spirit and scope of the present disclosure will become apparent to those skilled in the art from this detailed description.

BRIEF DESCRIPTION OF THE DRAWINGS

The aspects of the present disclosure may be better understood with reference to the following figures. The components in the figures are not necessarily to scale, emphasis instead being placed upon clearly illustrating the principles of the disclosure. Moreover, in the figures, like reference numerals designate corresponding parts throughout the several views.

In the figures.

The figures depict preferred embodiments of the present disclosure for purposes of illustration only. One skilled in the art will readily recognize from the following discussion that alternative embodiments of the structures and methods illustrated herein may be employed without departing from the principles of the present disclosure described herein.

DETAILED DESCRIPTION

Although the present disclosure will be described in terms of a specific embodiment, it will be readily apparent to those skilled in this art that various modifications, rearrangements and substitutions may be made without departing from the spirit of the present disclosure. The scope of the present disclosure is defined by the claims appended hereto.

Computed tomography (CT) is the science of creating two-dimensional cross-sectional images from projection images taken at different angles. CT utilizes a mathematical technique called reconstruction to achieve such task. Thus, CT is a mathematical process. A CT image is the result of breaking apart a three-dimensional structure and mathematically putting it back together and displaying it as a two-dimensional image on a display screen. The goal of the CT system is to accurately reproduce the internal structures of the body as two-dimensional cross-sectional images. Collecting many projections of an object and filtration of the x-ray beams are important factors in CT image formation. The development of spiral/helical CT allows continuous scanning while the patient is on a table and moves through a gantry aperture. The gantry is a movable frame that includes the x-ray tube having collimators, filters, detectors, data acquisition systems, and rotational components.

The present disclosure relates to an x-ray device, particularly in the form of a Computed Tomography (CT) scanner, which includes at least a radiation source and a beam filter. The beam filter may establish a number of intensity profiles in an associated detection area with minimal or even no changes to the spectrum of the radiation source. To achieve the aforementioned objective, it is proposed here to use two separate and distinct filtering elements to form the bow-tie wedge, as described below with reference to FIGS. 1-5B.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

Figure 1:
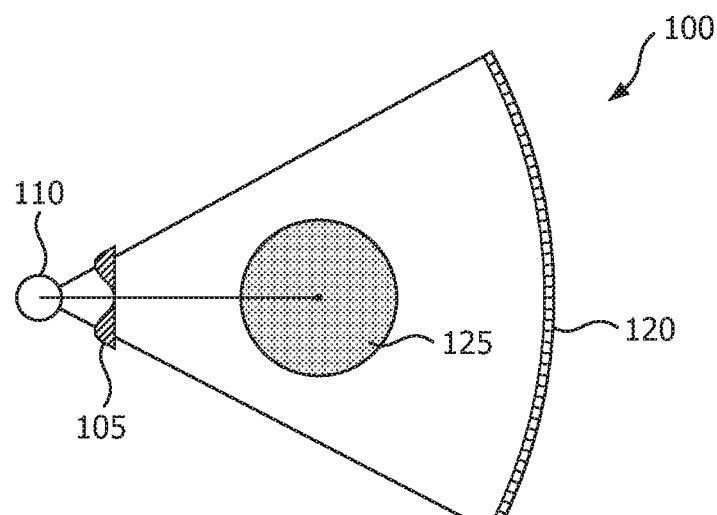
FIG. 1 illustrates a beam shaper located between a focal spot and a detector, according to the present disclosure.

Referring to FIG. 1, a beam shaper configuration 100 having a beam shaper 105 located between a focal spot or x-ray source 110 and a detector 120 is presented, according to the present disclosure.

The exemplary embodiments of the present disclosure allow for the modulation of incoming intensity of an x-ray beam such that the weighting that is used during reconstruction fits to the statistical significance of the measured data, which leads to improved dose utilization. This is achieved via the beam shaper 105, shown in FIG. 1.

The path that an x-ray beam travels from the x-ray source 110 to the detector 120 is referred to as a ray. After the x-ray beam passes through the object 125 being scanned, the detector 120 samples the beams intensity. The detector 120 reads each ray and measures the resultant beam attenuation. The attenuation measurement of each ray is termed a ray sum. A complete set of ray sums is referred to as a view of projection. It takes many views to create a CT image. The attenuation properties of each ray sum are accounted for and correlated with the position of each ray. Upon completion of attenuation measurement processing, the detector 120 has collected the projection or raw data. The more photons collected, the more accurate, i.e. the less noisy, the image reconstruction is. Details relating to the image reconstruction are described below.

The beam shaper 105 used in medical CT scanners (i.e., bow-tie filter) modulates the intensity of the x-ray beam as a function of the fan angle. The beam shaper 105 compensates for the different path lengths of the x-rays through the patient's body.

The purpose of the beam shaper 105, which has a bow-tie configuration, is to shape the x-ray beam such that more photons are emitted toward the iso-center of the system than to the periphery of the scan field of view (fov). This leads to a better dose utility, since rays near the iso-center typically are attenuated much more than peripheral rays. The shape of the beam along the rotation axis is typically designated such that a roughly homogeneous illumination of detector rows is achieved.

It is noted that during reconstruction, x-rays from different detector rows and columns are averaged because they essentially contain redundant information. In fact, the averaging is not performed in a way that the signal-to-noise (SNR) ratio is optimized. The weighting is tuned to balance SNR, motion artifacts, and cone-beam artifacts. This is achieved by using, for example, a so-called aperture weighted wedge reconstruction, where projection data with a larger aperture are weighted less than projection data with a small aperture. Of course, one skilled in the art may contemplate a plurality of different reconstruction algorithms for reconstructing the raw data.

Figure 2:
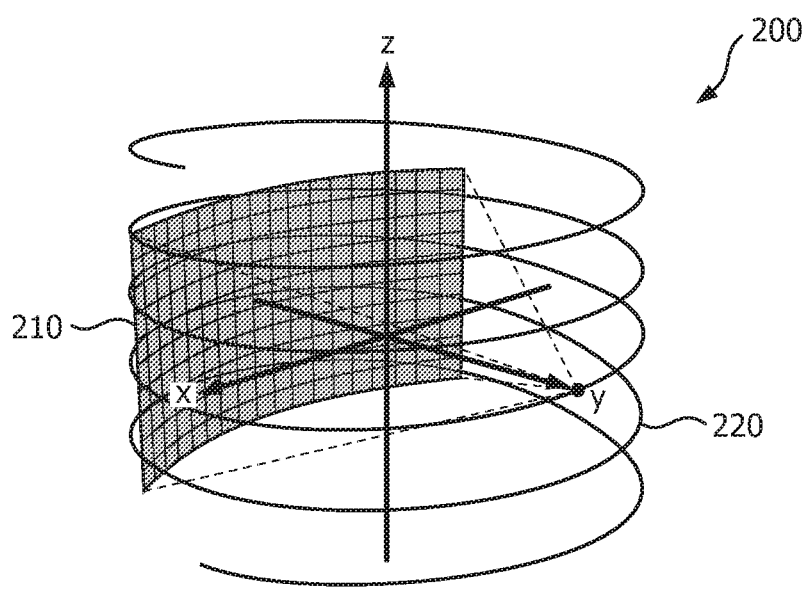
FIG. 2 illustrates acquisition geometry using a cylindrical detector and a helical system trajectory, according to the present disclosure.

FIG. 2 depicts acquisition geometry 200 using a cylindrical detector 210 and a helical system trajectory 220, according to the present disclosure.

Helical CT is CT technology involving movement in a helical pattern for the purpose of increasing coverage. CT beam types include parallel beams, fan beams, and cone beams. In cone beam CT, the x-ray beam is conical. Helical cone beam CT is a type of CT in which the x-ray source describes a helical trajectory relative to the object 125 (see FIG. 1), while a two-dimensional array of detectors measures the transmitted radiation on part of a cone of rays emanating from the x-ray source. During a cone beam CT scan, the scanner rotates around the patient's head or patient's body, obtaining hundreds if not thousands of distinct images. The scanning software collects the data and reconstructs it producing a digital volume composed of three-dimensional voxels of anatomical data that can be manipulated and visualized on a display screen.

Once the data has been acquired by the helical CT scan, the data is processed by using, for example, a form of tomographic reconstruction, which produces a series of cross-sectional images. The raw data acquired by the scanner includes multiple "projections" of the object 125 being scanned (see FIG. 1). These projections are effectively the Radon transformation of the structure of the object 125. Reconstruction, essentially involves solving the inverse Radon transformation. One skilled in the art may contemplate a plurality of different reconstruction algorithms to reconstruct the collected data in the exemplary embodiments of the present disclosure.

Figure 3A:
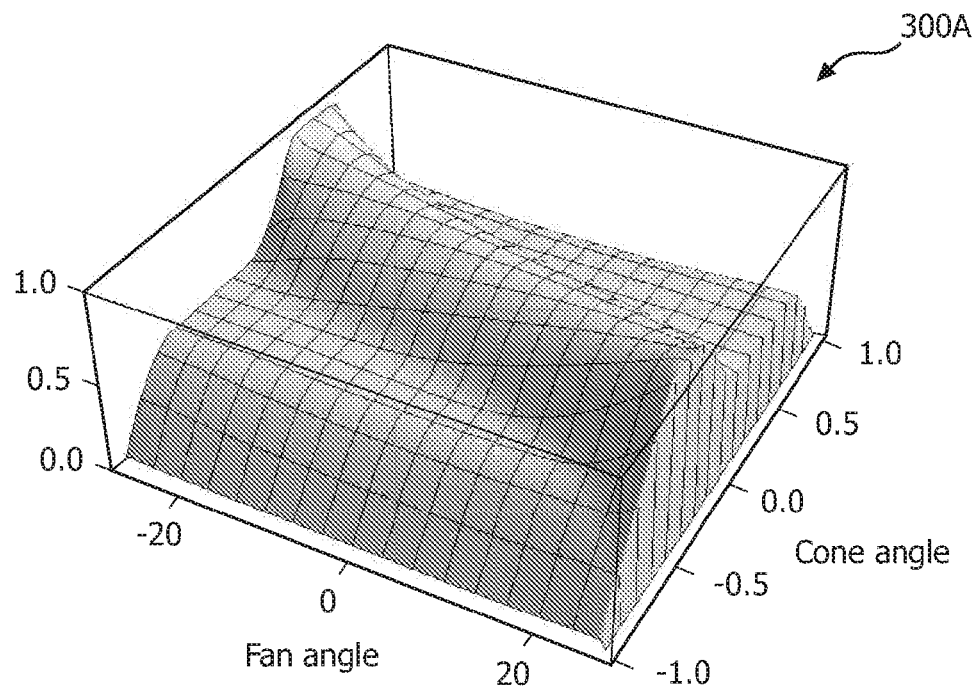
FIG. 3A illustrates an average normalized weight of a filtered sample for a helical CT scan.

FIG. 3A illustrates mean normalized weights for an example of a helical scan with a pitch factor of 1. These weights are obtained by reconstructing a single slice covering the entire field of view (fov).

FIG. 3A illustrates mean normalized weights for an example of a helical scan with a pitch factor of 1. These weights are obtained by reconstructing a single slice covering the entire field of view (fov). In order to ensure a one-to-one correspondence between the data and weights, nearest neighbor interpolation may be used during back-projection. The map of mean normalized weights shows the same basic feature as the non-normalized aperture weighting function, namely that the weights are largest in the central part and that the weights drop continuously to zero toward the upper and lower border of the detector 120 (see FIG. 1).

Figure 3B:
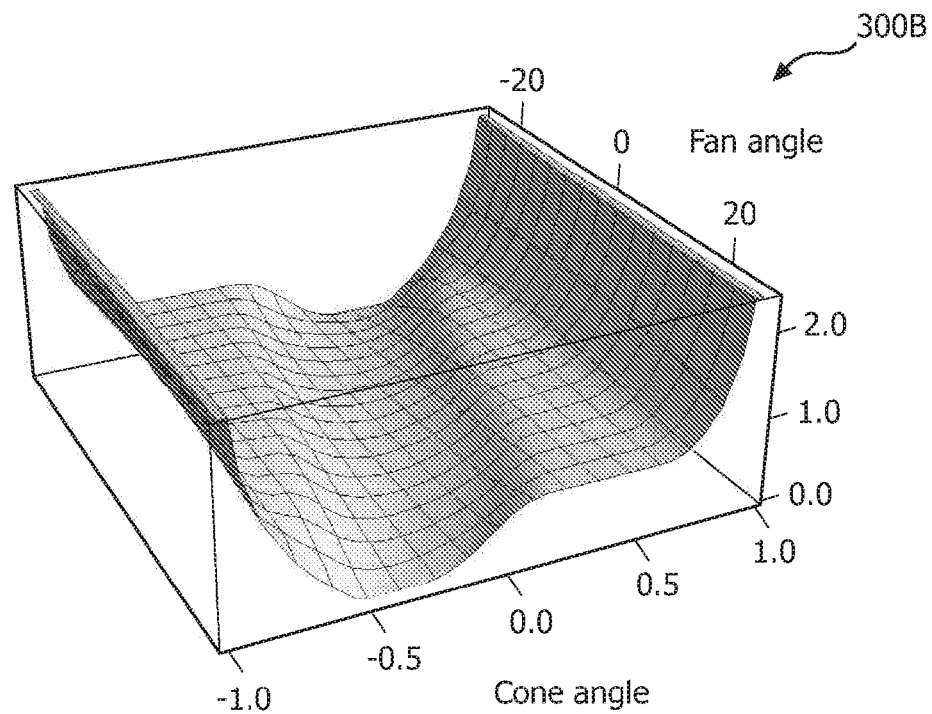
FIG. 3B illustrates a corresponding optimized thickness modulation of a matching bow-tie filter.

In FIG. 3B, the values on the z-axis are the desired attenuation values of the beam shaper 105 (see FIG. 1) over the detector panel. The shape ensures that the mean intensity toward each detector column is kept constant. Thus, on average there is no modulation in the fan direction. Thus, this bow-tie filter does not only reduce the average noise level in the reconstructed images, but also achieves a more homogeneous noise distribution across the fov. This inhomogeneous noise distribution in currently used systems, also referred to as "rotating noise," imposes some issues with noise reduction algorithms.

Therefore, in summary, referring to FIGS. 1-3B, the proposed beam shaper 105 is obtained with the following method. For a given acquisition and reconstruction algorithm, the actually used weights for each detector pixel are stored and averaged. The resulting map of mean weights is thus equal to the best distribution of the blank scan intensity. However, the slope of the valley, shown in FIG. 3B, is dependent on the helical pitch. This slope is optimized for one particular pitch. The optimization of the slope for each pitch limits the use of the bow-tie filter.

FIGS. 4A-5B illustrate an alternative method of achieving lower doses, where partitioning of the filter is presented. In other words, two overlaying or overlapping layers or filters are used to construct a bow-tie filter. One filter may be responsible for generating rays at large cone angles, whereas another filter may be used for generating "valley intensity."

Figure 4A:
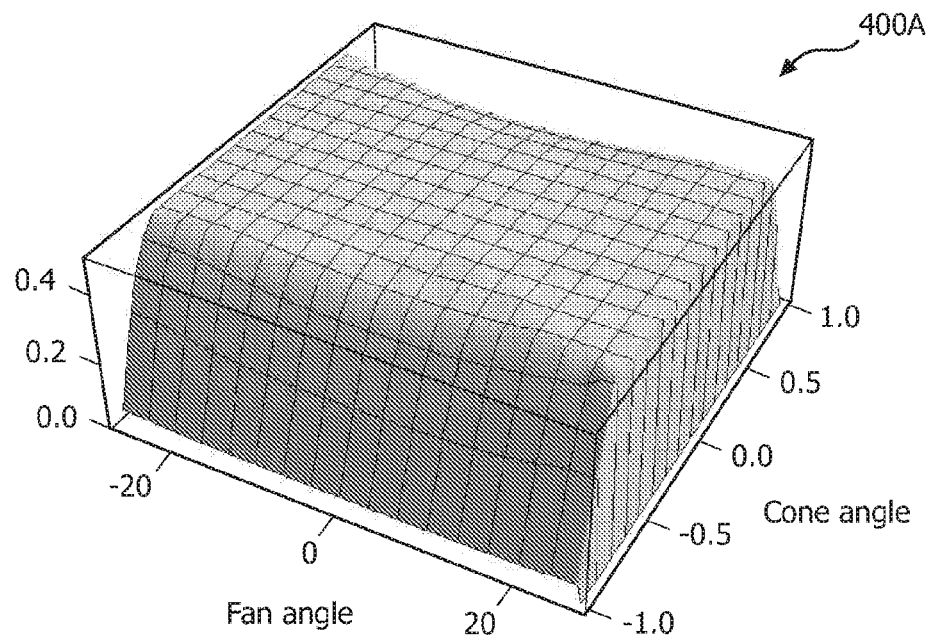
FIGS. 4A-4B illustrate partitioning of the mean weights for a helical acquisition and reconstruction in two parts, according to the present disclosure.
Figure 4B:
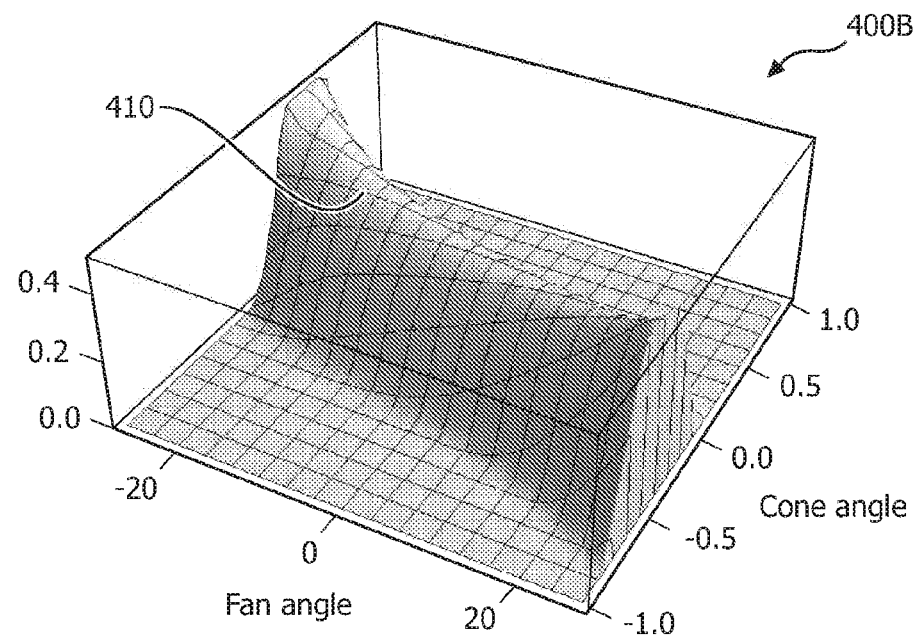

FIGS. 4A-4B illustrate partitioning of the mean weights for a helical acquisition and reconstruction in two parts 400A, 400B, according to the present disclosure.

In general, the optimal shape of the bow-tie filter depends on the scan mode. In particular, the bow-tie filter needs to be removable since reconstruction for axial scanning results in completely different average weights. Furthermore, the angulation of the area of high weights depends on the helical pitch. For instance, if the pitch is reversed, the average weights are mirrored. Therefore, in accordance with the exemplary embodiments of the present disclosure, a plurality of different bow-tie filters may be used, which are modular or replaceable or interchangeable. Stated differently, there are no geometrical constraints because a user may select a bow-tie filter from a plurality of bow-tie filters in order to achieve the desired helical pitch. For example, after a plurality of scans are performed with a first bow-tie filter, it may be removed and replaced with another bow-tie filter to achieve a different desired helical pitch.

In the exemplary embodiments of the present disclosure, it is proposed to partition the bow-tie filter into two sections or two layers or two portions. The first filter element or section is a background-wedge that mainly attenuates x-rays with a large aperture. In other words, the first filter element generates a small projecting weight for detector pixels having a large aperture. The second filter element or section creates a ridge 410 (see FIG. 4B) in the wedge or ridge profile. In other words, the second filter element generates higher back-projection widths than the first filter, thus resulting in smaller apertures. This partitioning of the mean weights for the case of a helical acquisition with a pitch of 1 is illustrated in FIGS. 4A-4B. The implication of this partitioning is that the bow-tie may be built by using two separate and distinct layers, at least one of the layers being removable or replaceable or interchangeable. It is noted that the first layer creates an intensity modulation corresponding to FIG. 4A. Moreover, the second layer may be mounted such that it can be rotated. By the rotation, the bow-tie filter can be adapted to different pitch helical values. Thus, the slope of the valley need not be optimized for one particular helical pitch because of the rotation of the second layer.

Figure 5A:
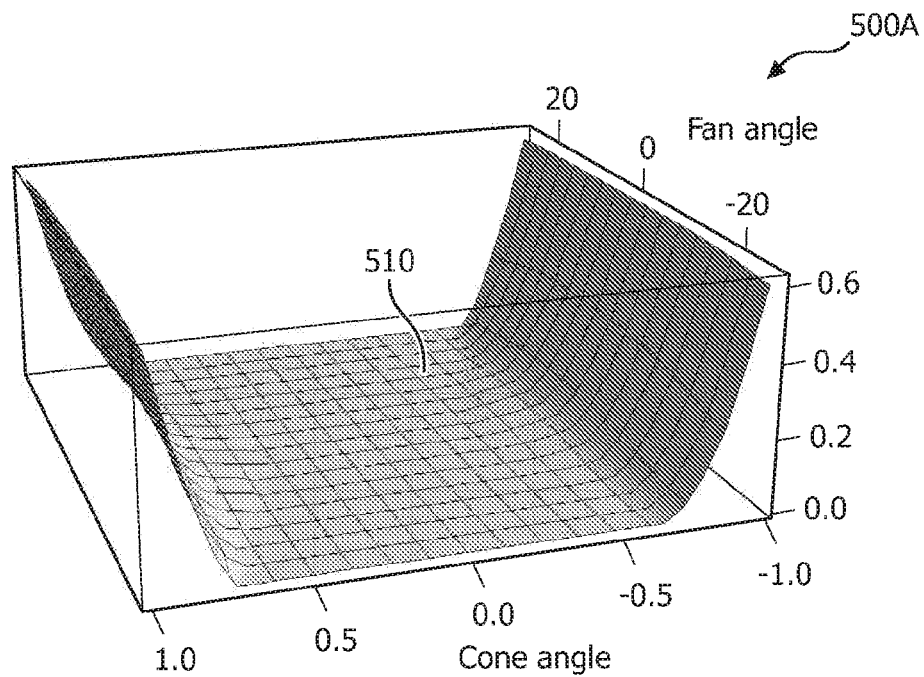
FIGS. 5A-5B illustrate required bow-tie filter thicknesses on two layers, according to the present disclosure.
Figure 5B:
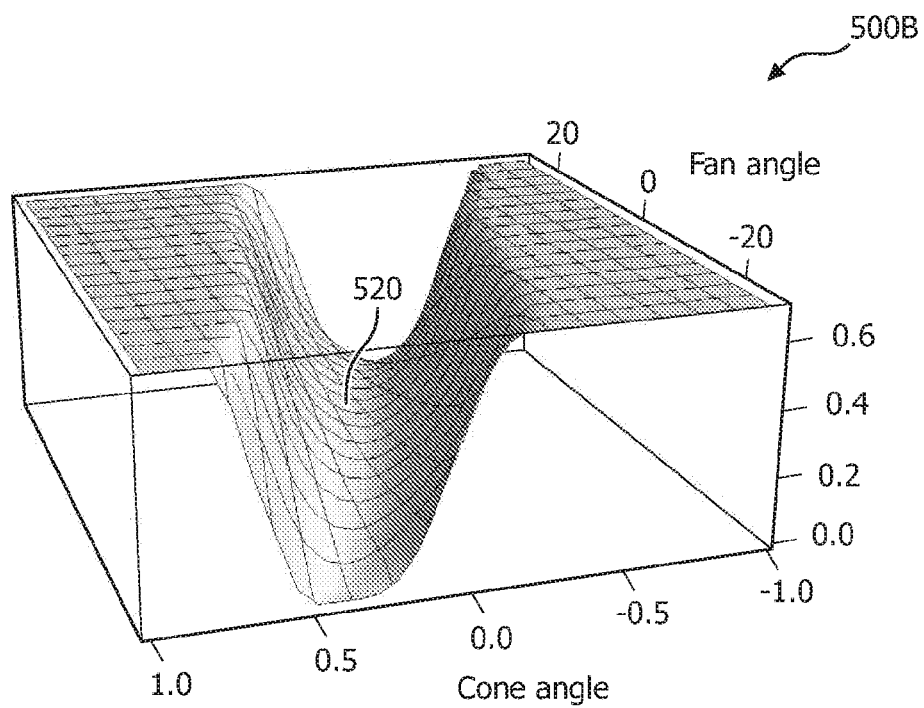

The first layer and the second layer are illustrated in FIGS. 5A-5B. FIGS. 5A-5B illustrate required bow-tie filter thicknesses on two layers 500A, 500B, according to the present disclosure. FIG. 5A illustrates the first layer 510, whereas FIG. 5B illustrates the second layer 520 (in an inverted configuration with respect to the image shown in FIG. 4B because of rotation of the second filter element). The first layer 510 is intended to be stationary (or can be completely removed from the beam shaper 105 for adaptation to axial scanning), whereas the second layer 520 is intended to rotate in order to adapt to the actual helical pitch of the acquisition. The second layer 520 is shown inverted in FIG. 5B compared to the image shown in FIG. 4B because of rotation of the second filter element.

In an alternative embodiment, the bow-tie filter may be a MAD (multiple aperture device) filter. A MAD filter delivers high-beam intensity modulation (e.g., greater than 95%), has a small thickness (e.g., less than 15 mm), provides no beam hardening, and provides no scattering of radiation. A MAD filter modulates x-ray beam intensity by transmitting the beam through apertures. The intensity of the transmitted beam is a function of the area of the apertures. MAD has apertures of varying sizes that modulate the intensity of the transmitted beam. As noted, the modulation of the beam intensity does not result in any beam hardening.

Moreover, the apertures are slits in a plate, the plate constructed of a high-density, high Z material (e.g., tungsten). In other words, MAD shapers are constructed of thin metal plates with a number of slits, where the transmission of the filter is controlled by the width of the slits. The thickness of the plate is such that the plate attenuates more than 99.9% of the incident beam. Further, the modulation of the beam intensity does not result in any scattered radiation and the slits are focused on the x-ray focal spot. As a result, the apertures may provide 0% to 95% intensity modulation.

In summary, bow-tie filters absorb low intensity photons before reaching the patient. X-ray beams are polychromatic in nature, which means an x-ray beam includes photons of several different energies. Ideally, the x-ray beam should be monochromatic or composed of photons having the same intensity. Filtration of the x-ray beam results in a more uniform beam. The more uniform the beam, the more accurate the attenuation values or CT numbers are for the scanned anatomical region. As a result, the exemplary embodiments of the present disclosure propose a filter assembly for use in a helical CT system, where two separate and distinct filter elements or layers are presented. The two filter elements or sections combine to form the bow-tie filter for accommodating a plurality of different helical pitches desired by a user. It is noted that the second layer of the bow-tie filter is not rotated during a scan, but remains fixed. However, during setup of the system, the second layer of the bow-tie element may be rotated or removed or replaced or adjusted to accommodate different helical pitch angles.

In summary, MAD bow-tie filters may be presented in lieu of Teflon-based bowtie filters. The MAD filter modulates the beam intensity in medical CT systems. The MAD filter is positioned in the x-ray beam of a CT system between the x-ray tube and the patient. The MAD filter has different size apertures, such that the intensity of the x-ray beam transmitted through MAD varies according to the area of the apertures. In one exemplary embodiment, the apertures may be arranged such that the largest apertures are positioned on the central axis of the x-ray beam, thus enabling the largest percentage transmission at the central axis. The size of the apertures decreases as the distance of the apertures from the beam's central axis increases. The transmission of the x-ray beam decreases as a function of the distance from the central axis.

Finally, it is pointed out that in the present application the term "comprising" does not exclude other elements or steps, that "a" or "an" does not exclude a plurality, and that a single processor or other unit may fulfill the functions of several means. The present disclosure resides in each and every novel characteristic feature and each and every combination of characteristic features. Moreover, reference signs in the claims shall not be construed as limiting their scope.

The foregoing examples illustrate various aspects of the present disclosure and practice of the methods of the present disclosure. The examples are not intended to provide an exhaustive description of the many different embodiments of the present disclosure. Thus, although the foregoing present disclosure has been described in some detail by way of illustration and example for purposes of clarity and understanding, those of ordinary skill in the art will realize readily that many changes and modifications may be made thereto without departing form the spirit or scope of the present disclosure.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A filter assembly for use in a helical computed tomography (CT) system having an x-ray source for projecting x-ray beams along a projection axis, the filter assembly comprising:
    a first filter element for attenuating at least a portion of the x-ray beams, the first filter element constructed as a background-wedge for attenuating x-rays having a large aperture; and
    a second filter element for attenuating at least a portion of the x-ray beams, the second filter element constructed to create a ridge, wherein the second filter element is rotated with respect to the filter assembly and the rotation of the second filter element allows for adaptation to different helical pitch values.

2. The filter assembly according to claim 1, wherein the second filter element is adapted to remain fixed during a scan and for being rotated during setup to accommodate the different helical pitch values.

3. The filter assembly as in claim 2, wherein the first filter element remains stationary.

4. The filter assembly as in claim 2, wherein the first and second filter elements are positioned between the x-ray source and a detector for reconstructing an image of an object onto which the x-ray beams are projected upon.

5. The filter assembly according to claim 4, wherein reconstruction occurs with one or more reconstruction algorithms.

6. The filter assembly as in claim 1, wherein the ridge of the second filter element is adapted for creating a valley in an x-ray attenuation profile of the filter assembly as a function of a cone angle and a fan angle, such that the rotation of the second filter element determines a slope with respect to the cone angle in the valley of the x-ray attenuation profile to accommodate the different helical pitch values.

7. The filter assembly as in claim 1, wherein the first and second filter elements combine to form a substantially bow-tie shaped filter.

8. The filter assembly as in claim 1, wherein the first and second filter elements result in a partitioning of mean weights of the x-ray beams projected onto an object.

9. A filter assembly for use in a helical computed tomography (CT) system, the filter assembly comprising:
    a first filter layer having a first shape; and
    a second filter layer having a second shape, the second shape being different than the first shape;
    wherein the second filter layer is adapted and dimensioned to rotate with respect to or be adjusted in relation with or be removed from the filter assembly to accommodate a plurality of different helical pitch values.

10. The filter assembly according to claim 9, wherein the first shape is a wedge and the second shape is a substantially ridge-shaped configuration.

11. The filter assembly as in claim 9, wherein the first filter layer remains stationary.

12. The filter assembly as in claim 9, wherein the first and second filter layers are used for reconstructing an image of an object onto which the x-ray beams from an x-ray source are projected upon.

13. The filter assembly according to claim 12, wherein reconstruction occurs with one or more reconstruction algorithms.

14. The filter assembly as in claim 9, wherein the first and second filter layers combine to form a substantially bow-tie shaped filter.

15. The filter assembly as in claim 9, wherein the first and second filter layers result in a partitioning of mean weights of x-ray beams projected onto an object from an x-ray source.

16. A method for reducing radiation exposure when using a helical computed tomography (CT) system, the method comprising:
    positioning a first filter element and a second filter element in a filter assembly between a patient and an x-ray source emitting x-ray beams;
    attenuating a portion of the x-ray beams via the first filter element, the first filter element being a background-wedge for attenuating x-ray beams having a large aperture; and attenuating a portion of the x-ray beams via the second filter element, the second filter element configured to create a ridge;

rotating the second filter element with respect to the filter assembly, which allows for adaptation of different helical pitch values.

17. The method according to claim 16, wherein the first filter element remains stationary, whereas the second filter element remains fixed during a scan and rotates during setup to accommodate the different helical pitch values.

18. The method as in claim 16, wherein the second filter element adapts for creating a valley in an x-ray attenuation profile of the filter assembly as a function of a cone angle and a fan angle, such that the rotation of the second filter element determines a slope with respect to the cone angle in the valley of the x-ray attenuation profile to accommodate the different helical pitch values.

19. The method as in claim 16, wherein the first and second filter elements are used for reconstructing an image of an object onto which the x-ray beams from the x-ray source are projected upon, the reconstruction occurring with one or more reconstruction algorithms.

20. The method as in claim 16, wherein the first and second filter elements result in a partitioning of mean weights of the x-ray beams projected onto the patient from the x-ray source.

* * * * *